(12) United States Patent
Jacobs et al.

(10) Patent No.: US 6,942,855 B2
(45) Date of Patent: Sep. 13, 2005

(54) VIRAL VECTORS HAVING REDUCED VIRULENCE

(75) Inventors: Bertram Jacobs, Tempe, AZ (US); Jeffrey Langland, Mesa, AZ (US); Sangeetha Vijaysri, San Diego, CA (US)

(73) Assignee: Arizona Board of Regents, Temp, AZ (US)

( * ) Notice: Subject to any disclaimer, the term of this patent is extended or adjusted under 35 U.S.C. 154(b) by 0 days.

(21) Appl. No.: 10/830,547

(22) Filed: Apr. 23, 2004

(65) Prior Publication Data

US 2005/0042206 A1 Feb. 24, 2005

Related U.S. Application Data

(62) Division of application No. 09/837,998, filed on Apr. 19, 2001, now Pat. No. 6,750,043.

(51) Int. Cl.[7] .................. A61K 48/00; C12N 15/863
(52) U.S. Cl. .................. 424/93.2; 424/93.1; 424/93.6
(58) Field of Search ..................... 435/320.1, 69.1; 424/93.1, 93.2, 93.6

(56) References Cited

U.S. PATENT DOCUMENTS

| | | | |
|---|---|---|---|
| 6,004,777 A | 12/1999 | Tartaglia et al. | ............ 435/69.1 |
| 6,372,455 B1 | 4/2002 | Jacobs et al. | ............... 435/69.1 |
| 2002/0110565 A1 | 8/2002 | Jacobs et al. | |

FOREIGN PATENT DOCUMENTS

| | | |
|---|---|---|
| WO | 9955910 | 11/1999 |
| WO | 0062735 | 10/2000 |
| WO | 0073487 | 12/2000 |

OTHER PUBLICATIONS

Chang et al., J. Virol., 1995, vol. 69, No. 10, pp. 6605–6608.*

Chang et al., PNAS, 1992, vol. 89, pp. 4825–4829.*

U.S. Appl. No. 09/887,295, filed Aug. 15, 2002, Jacobs et al.

Brandt et al., "Both Carboxy– and Amino–Terminal Domains of the Vaccinia Virus Interferon Resistance Gene, E3L, Are Required for Pathogenesis in a Mouse Model", J. Virology 75:850–856, 2001.

Shors et al., "Complementation of Vaccinia Virus Deleted of the E3L Gene by Mutants of E3L", Virology 239:269–276, 1997.

Kibler et al., "Double–Stranded RNA Is a Trigger for Apoptosis in Vaccinia Virus–Infected Cells" Journal of Virology 71:1992–2003, 1997.

Beattie et al., "Host–Range Restriction of Vaccinia Virus E3L—Specific Deletion Mutants", Viru Genes, 1996, vol. 12, pp. 89–94.

Beattie et al., "Reversal of the Interferon–Sensitive Phenotype of a Vaccinia Virus Lacking E3L by Expression of the Reovirus S4 Gene", Journal of Virology, vol. 69, No. 1, Jan. 1995, pp. 499–505.

Chang et al., "Indentification of a Conserved Motif That is Necessary for Binding of the Vaccinia Virus E3L Gene Products to Double–Stranded RNA", Virology 194:537–547, 1993.

* cited by examiner

*Primary Examiner*—David Guzo
(74) *Attorney, Agent, or Firm*—Baker Botts LLP

(57) ABSTRACT

The present invention provides recombinant vaccinia virus having a deletion of the region encoding the C-terminal seven amino acids of the E3L gene product and comprising exogenous DNA. Compositions comprising the recombinant vaccinia virus and methods of use thereof are also provided.

4 Claims, 4 Drawing Sheets

Fig. 3

VIRAL VECTORS HAVING REDUCED VIRULENCE

This application is a Division of U.S. patent application Ser. No. 09/837,998, filed Apr. 19, 2001, now U.S. Pat. No 6,750,043.

BACKGROUND OF THE INVENTION

Vaccinia virus is a member of the poxvirus family of DNA viruses. Poxviruses including vaccinia virus are extensively used as expression vectors since the recombinant viruses are relatively easy to isolate, have a wide host range, and can accommodate large amounts of DNA.

The vaccinia virus genome contains nonessential regions into which exogenous DNA can be incorporated. Exogenous DNA can be inserted into the vaccinia virus genome by well-known methods of homologous recombination. The resulting recombinant vaccinia viruses are useful as vaccines and anticancer agents.

The use of vaccinia virus recombinants as expression vectors and particularly as vaccines and anticancer agents raises safety considerations associated with introducing live recombinant viruses into the environment. Virulence of vaccinia virus recombinants in a variety of host systems has been attenuated by the deletion or inactivation of certain vaccinia virus genes that are nonessential for virus growth. However, there remains a need in the art for the development of vectors that have reduced pathogenicity while maintaining desirable properties of wild-type virus, such as host range, and active protein synthesis of a desired gene product.

SUMMARY OF THE INVENTION

The present invention provides methods of use of a recombinant vaccinia virus having a mutation in or near the region of the E3L gene that encodes a double stranded (ds)-RNA binding domain. The invention further provides an expression vector comprising the recombinant vaccinia virus and exogenous DNA.

BRIEF DESCRIPTION OF THE DRAWING

FIG. 3 is a graph depicting tissue distribution of vaccinia virus after intranasal injection.

DETAILED DESCRIPTION OF THE INVENTION

Figure 1:
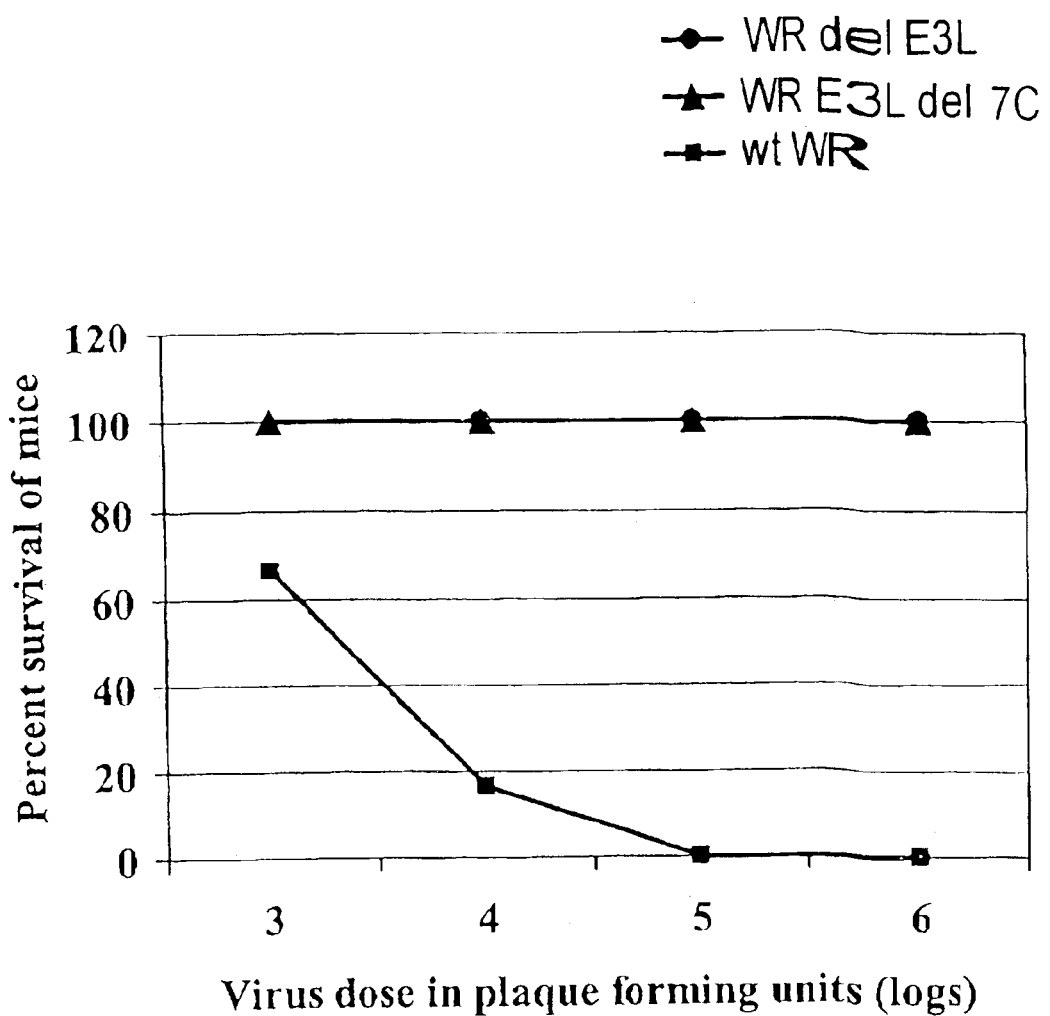
FIG. 1 is a graph depicting survival of mice following intranasal injection with vaccinia virus.

The E3L gene product of the vaccinia virus is a 190 amino acid polypeptide. The E3L gene codes for several functions including a dsRNA-binding protein, a Z-DNA-binding protein, and dimerization. Amino acids 118–190 have been implicated in dsRNA binding, as disclosed by Kibler et al. (1997) *J. Virol.* 71: 1992, incorporated herein by reference. Amino acid numbering as used herein is adopted from Goebel et al. (1990) *Virology* 179: 247–66, 577–63, the disclosure of which is incorporated herein by reference.

It has been discovered in accordance with the present invention that recombinant vaccinia viruses having mutations in or near the region encoding the dsRNA-binding domain have decreased pathogenesis in mammals relative to wild-type vaccinia virus. When administered intranasally, the recombinant viruses of the present invention replicate to high titers in nasal tissues, but do not spread to the lung or brain. When administered directly into the brain, the recombinant viruses exhibit decreased neurovirulence relative to wild-type vaccinia virus.

The mutations encompassed by the present invention are those which decrease, but do not abolish, binding of the mutant E3L gene product to dsRNA relative to the native E3L gene product. The ability of the E3L gene product to bind to dsRNA can be determined by binding assays known in the art and disclosed for example by Clang et al. (1993) *Virology* 194:537, the disclosure of which is incorporated herein by reference. A decrease in dsRNA binding is defined herein as one that is detectable by an assay described by Chang et al., id.

The term mutation, as used herein, includes deletions, substitutions and point mutations. In a preferred embodiment of the present invention, the mutation is a deletion of the region encoding amino acids 184–190 of the E3L gene product, designated herein as E3L del 7C.

The present invention further provides recombinant vaccinia viral vectors comprising the recombinant vaccinia virus described above and further containing exogenous, i.e., nonvaccinia virus, DNA. Exogenous DNA may encode any desired product, including for example, an antigen, an anticancer agent, or a marker or reporter gene product. The recombinant vaccinia virus may further have deletions or inactivations of nonessential virus-encoded gene functions. Nonessential gene functions are those which are not required for viral replication in a host cell. The exogenous DNA is preferably operably linked to regulatory elements that control expression thereof. The regulatory elements are preferably derived from vaccinia virus.

The recombinant vaccinia virus of the present invention may be constructed by methods known in the art, and preferably by homologous recombination. Standard homologous recombination techniques utilize transfection with DNA fragments or plasmids containing sequences homologous to viral DNA, and infection with wild-type or recombinant vaccinia virus, to achieve recombination in infected cells. Conventional marker rescue techniques may be used to identify recombinant vaccinia virus. Representative methods for production of recombinant vaccinia virus by homologous recombination are disclosed by Piccini et al. (1987) *Methods in Enzymology* 153: 545, the disclosure of which is incorporated herein by reference.

For example, the recombinant vaccinia virus of a preferred embodiment of the present invention may be constructed by infecting host cells with vaccinia virus from which the E3L gene has been deleted, and transfecting the host cells with a plasmid containing a nucleic acid encoding amino acids 1–183 of the E3L gene product flanked by sequences homologous to the left and right arms that flank the vaccinia virus E3L gene. The vaccinia virus used for preparing the recombinant vaccinia virus of the invention may be a naturally occurring or engineered strain. Strains useful as human and veterinary vaccines are particularly preferred and are well-known and commercially available. Such strains include Wyeth, Lister, WR, and engineered deletion mutants of Copenhagen such as those disclosed in U.S. Pat. No. 5,762,938, which is incorporated herein by reference. Recombination plasmids may be made by standard methods known in the art. The nucleic acid sequences of the vaccinia virus E3L gene and the left and right flanking arms are well-known in the art, and may be found for example, in Earl et al. (1993) in *Genetic Maps: locus maps of complex genomes*, O'Brien, ed., Cold Spring Harbor Laboratory Press, 1.157 the disclosure of which is incorporated by reference, and Goebel et al. (1990), supra. The amino acid numbering used herein is adopted from Goebel et al. (1990), supra. The vaccinia virus used for recombination may contain other deletions, inactivations, or exogenous DNA as described hereinabove.

Following infection and transfection, recombinants can be identified by selection for the presence or absence of markers on the vaccinia virus and plasmid. Recombinant vaccinia virus may be extracted from the host cells by standard methods, for example by rounds of freezing and thawing.

The resulting recombinant vaccinia virus may be further modified by homologous recombination to provide other deletions, inactivations, or to insert exogenous DNA.

It has been discovered in accordance with the present invention that a recombinant vaccinia virus having a deletion of the DNA encoding a C-terminal portion of the E3L gene product, and preferably amino acids 184–190 of the E3L gene product, maintains viral replication, protein synthesis and inteferon-resistance that is indistinguishable from wild-type virus, but has remarkably reduced pathogenicity in mice relative to wild-type vaccinia virus of the same strain.

The present invention further provides a composition comprising the recombinant vaccinia viral vector of the invention and a carrier. The term carrier as used herein includes any and all solvents, diluents, dispersion media, antibacterial and antifungal agents, microcapsules, liposomes, cationic lipid carriers, isotonic and absorption delaying agents, and the like.

The recombinant vaccinia viruses and compositions of the present invention may be used as expression vectors in vitro for the production of recombinant gene products, or as delivery systems for gene products, as human or veterinary vaccines, or anticancer agents. Such utilities for recombinant vaccinia viruses are known in the art, and disclosed for example by Moss (1996) "Poxviridae: The Viruses and Their Replication" in *Virology*, Fields et al., eds., Lippincott-Raven, Philadelphia, pp. 2637–2671, incorporated herein by reference.

The present invention further provides a method of making a recombinant gene product comprising subjecting a recombinant vaccinia viral vector comprising a vaccinia virus from which at least the region encoding amino acids 184–190 of the E3L gene product has been deleted and further comprising exogenous DNA that encodes the recombinant gene product operably linked to the control of regulatory elements that control expression thereof, to conditions whereby said recombinant gene product is expressed, and optionally recovering the recombinant gene product. In a preferred embodiment, the recombinant gene product is an antigen that induces an antigenic and/or immunogenic response when the gene product or a vector that expresses it is administered to a mammal.

All references cited herein are incorporated in their entirety.

The following nonlimiting examples serve to further illustrate the invention.

EXAMPLE 1

Construction of Recombinant Vaccinia Virus

The plasmid pMPE3ΔGPTMCS (described by Kibler et al. (1997) *J. Virol.* 71: 1992, incorporated herein by reference) was used for recombining a truncated E3L gene having a deletion of the 7C-terminal amino acids into the E3L locus of the WR strain of vaccinia virus. The recombination plasmid pMPE3ΔGPT is a derivative of pBSIISK (Stratagene, La Jolla, Calif.) that has had the β-galactosidase sequences deleted, and that contains sequences homologous to the left and right arms flanking the vaccinia virus E3L gene, but that lacks the E3L gene itself. The recombination plasmid contains the *E. coli* gpt gene outside the E3L flanking arms and thus allows for selection of transfected cells by treatment with mycophenolic acid (MPA). The plasmid pMPE3ΔGPT was altered by the addition of a multiple cloning site to create pMPE3ΔGPTMCS.

The E3L mutant gene Δ7C (described by Chang et al. (1993) *Virology* 194: 537, the disclosure of which is incorporated by reference) was cloned into the pMPE3ΔGPTMCS recombination plasmid. The E3L Δ7C fragment encodes amino acids 1–183 of the E3L gene product as numbered by Goebel et al. (1990) supra, and has a deletion of the DNA encoding the C-terminal amino acids 184–190. The plasmid resulting from the cloning of the E3L Δ7C fragment into pMPE3ΔGPTMCS is designated pMP-Δ7C.

In vivo recombination with WRΔE3L (WR strain of vaccinia virus in which the E3L gene was replaced by the lacZ gene) and selection of recombinants was performed as described by Kibler et al. (1997) *J. Virol* 71: 1992 to provide WRE3LΔ7C. WRΔE3L was obtained by replacing the E3L gene from the WR strain of vaccinia virus with the lacZ gene by homologous recombination with pMPE3ΔGPT (Kibler et al. (1997) *J. Virol.* 71:1992) in which the lacZ gene was inserted between the E3L flanking arms.

EXAMPLE 2

Infection with WR, WRE3LΔ7C and WRΔE3L

Wild-type vaccinia virus of the WR strain (wt WR) and variants WRΔE3L and WRE3LΔ7C as described in Example 1 were assessed for pathogenicity as follows.

Groups of five c57b16 mice at four weeks of age were infected with different doses ($10^3$ plaque forming units (pfu), $10^4$ pfu, $10^5$ pfu and $10^6$ pfu) of WR, WRΔE3L and WRE3LΔ7C by intranasal administration, and observed daily for death. Groups of six c57b16 mice at four weeks of age were infected with the same doses of these viruses by intracranial injection and observed daily for death.

Figure 2:
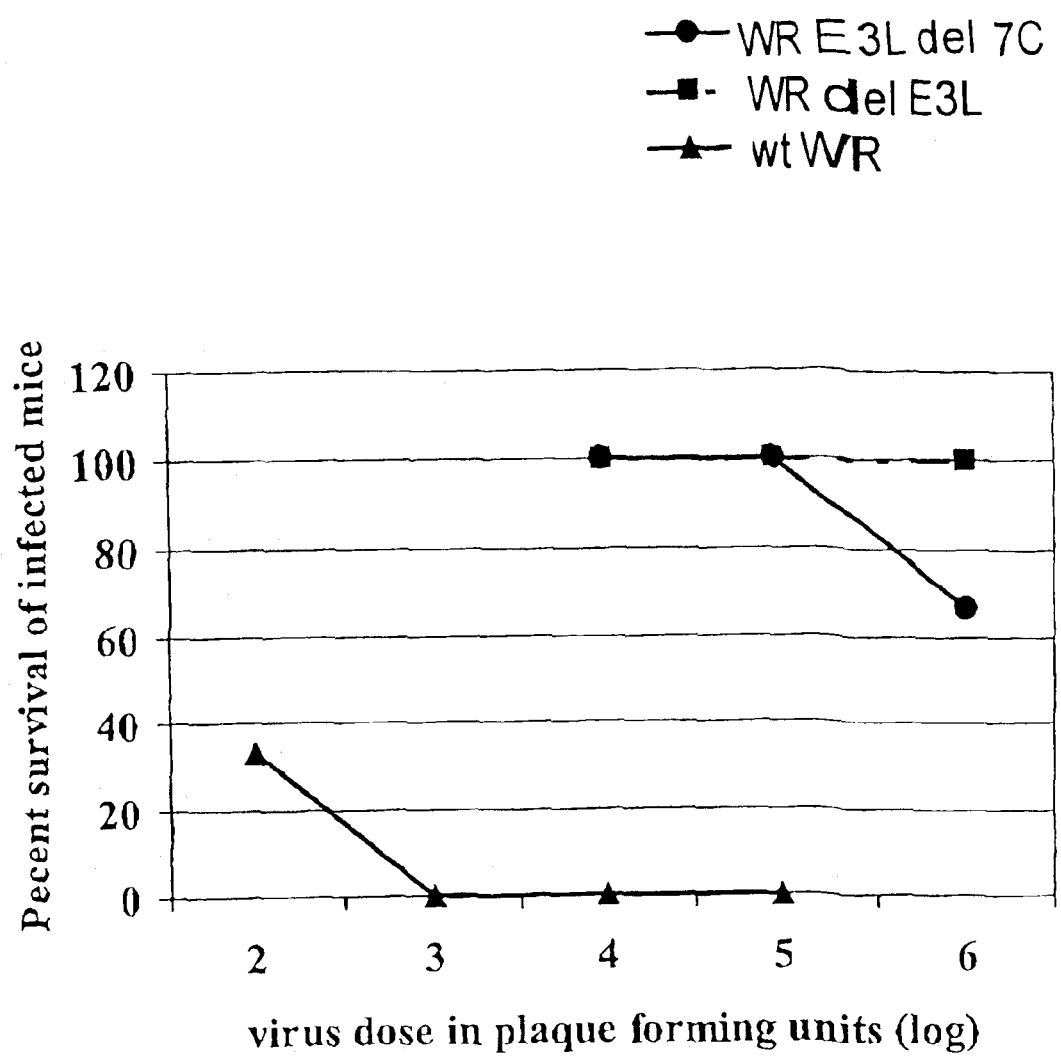
FIG. 2 is a graph depicting survival of mice following intracranial injection with vaccinia virus.

As shown in FIG. 1, intranasal inoculation with WR was lethal at a dose of $10^3$ pfu, whereas no pathogenicity could be detected with WRΔE3L or WRE3LΔ7C even at the highest dose ($10^6$ pfu). Similarly, as show in FIG. 2, intracranial injection with WR was lethal at a dose of $10^3$ pfu, whereas no pathogenesis could be detected with the variants at a dose of $10^5$ pfu.

EXAMPLE 3

Tissue Distribution of Virus

Figure 3:
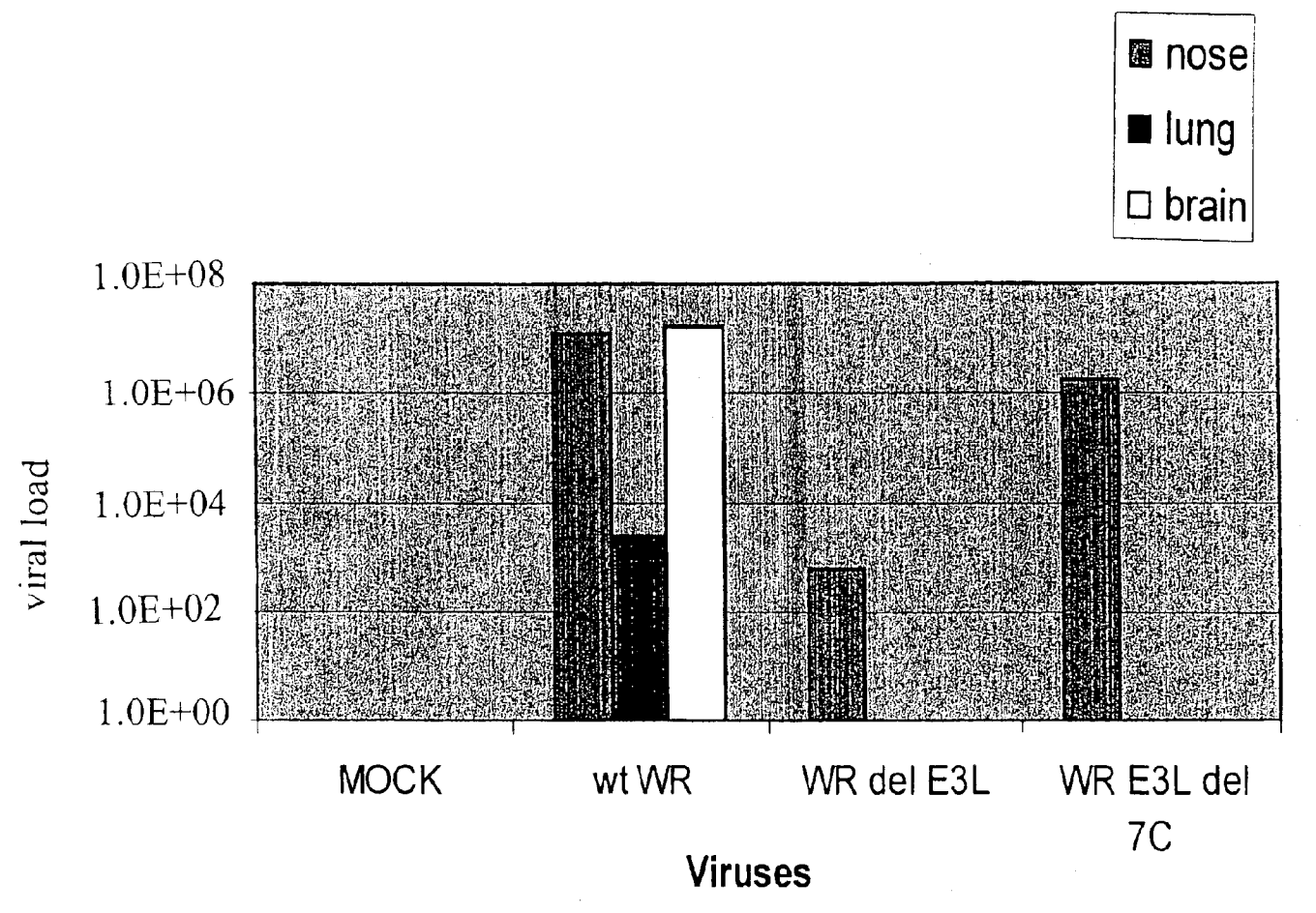

Groups of three c57b16 mice were injected with $10^6$ pfu of wt WR, WRΔE3L and WRE3LΔ7C by intranasal administration. Nasal turbinates, lung and brain were harvested, processed and titrated in an RK-13 cell line five days post infection. As shown in FIG. 3, wt WR was detected in nasal turbinates, lung and brain. The WRE3LΔ7C was detected in nasal turbinates, but unlike wt WR, it did not spread to lung and brain following intranasal injection.

EXAMPLE 4

Vaccination with WRE3LΔ7C

Figure 4:
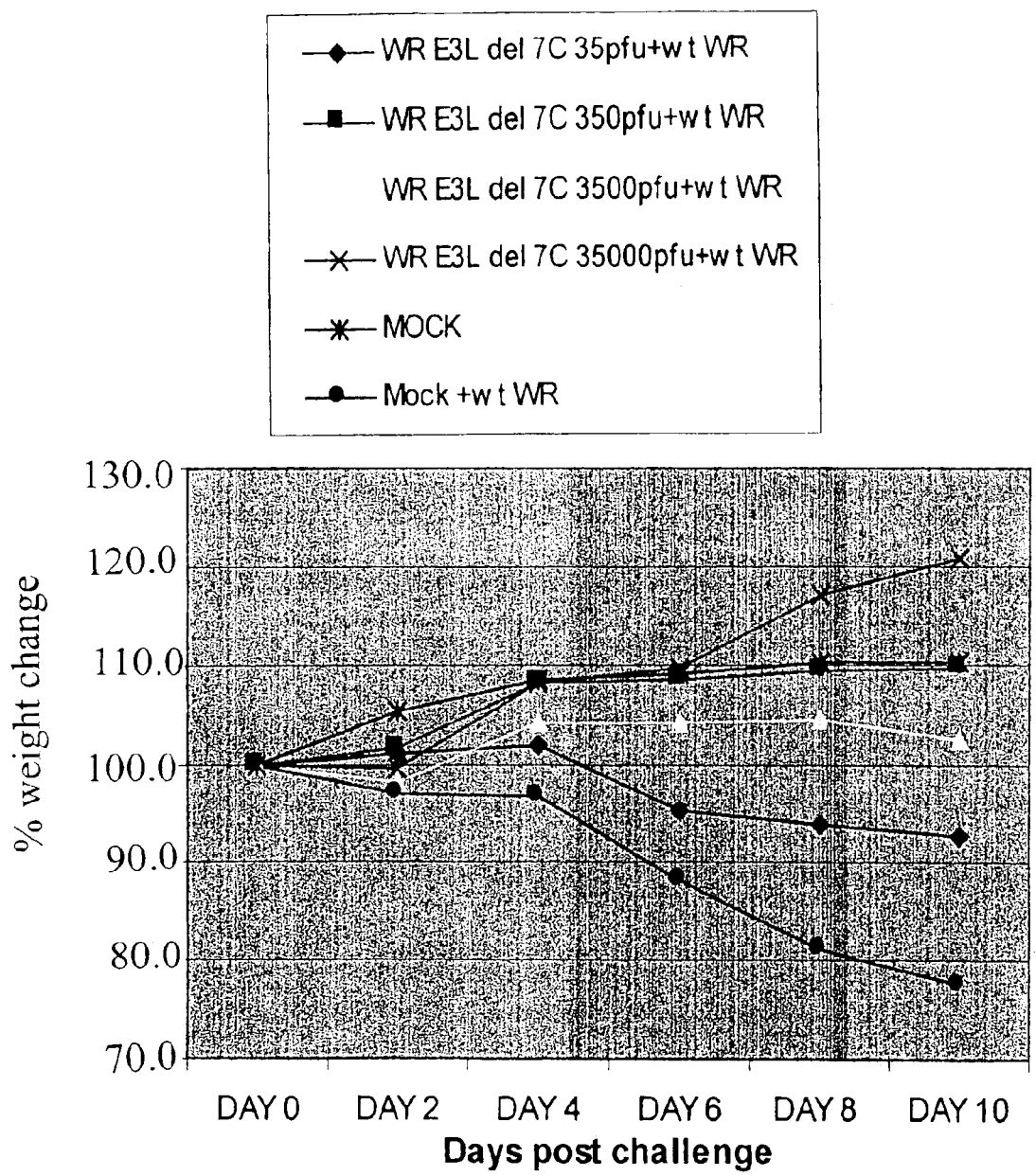
FIG. 4 is a graph depicting weight change in vaccinated and unvaccinated mice after challenge with wild-type virus.

Groups of five c57b16 mice were immunized with different doses (ranging from 35 to 35,000 pfu) of WRE3LΔ7C. One month later the immunized mice and the unimmunized controls (mock) were challenged with a million pfu of wt WR. Weight loss was used as an indicator of disease due to wt WR. As shown in FIG. 4, severe weight loss was observed in the unimmunized control while all the 5 immunized mice recorded normal weight gain following challenge. 350 pfu of the recombinant virus was sufficient to protect mice against infection with wt WR.

We claim:

1. A method of inducing an immune response in a subject comprising introducing to the subject an expression vector comprising a vaccinia virus with reduced pathogenicity in an animal host, which comprises an E3L gene that has a deletion of the region encoding amino acids 184–190 of the E3L protein and encodes a protein that binds dsRNA; and exogenous DNA operably linked to regulatory elements that control expression of said exogenous DNA.

2. The method of claim 1, wherein the immune response is a wild-type vaccinia virus immune response.

3. The method of claim 1, wherein said exogenous DNA encodes an antigen.

4. The method of claim 1, wherein one or more non-essential virus-encoded gene functions have been deleted from the vaccinia virus.

* * * * *